United States Patent [19]
Balazs et al.

[11] Patent Number: 5,252,558
[45] Date of Patent: Oct. 12, 1993

[54] PENTAPEPTIDE HAVING SPECIFIC INHIBITING EFFECT ON EPIDERMAL CELL PROLIFERATION, THE SALTS THEREOF, PHARMACEUTICAL COMPOSITIONS COMPRISING THE SAME AND A PROCESS FOR THE PREPARATION OF THE PENTAPEPTIDE AND THE PHARMACEUTICAL COMPOSITIONS

[75] Inventors: András Balazs; Tamás Szirtes; Istvá Schon, all of Budapest, Hungary; Lajos Kisfaludy, deceased, late of Budapest, Hungary, by András Kisfaludy, Márta Kisfaludy Maria Kisfaludy nee Makovitz, heirs

[73] Assignee: Richter Gedeon Vegyeszeti Gyar RT, Budapest, Hungary

[21] Appl. No.: 750,330

[22] Filed: Aug. 27, 1991

[30] Foreign Application Priority Data

Sep. 3, 1990 [HU] Hungary ............................. 5744/90

[51] Int. Cl.$^5$ ..................... A61K 37/02; C07K 7/06
[52] U.S. Cl. ..................... 514/17; 530/330; 930/320
[58] Field of Search ............. 930/320; 530/330; 514/17

[56] References Cited

U.S. PATENT DOCUMENTS 4,386,073 5/1983 Kisfauldy et al. ............. 514/18

FOREIGN PATENT DOCUMENTS 0099056 1/1984 European Pat. Off. .
2514381 10/1975 Fed. Rep. of Germany .
2753 3/1990 World Int. Prop. O. ......... 530/330

OTHER PUBLICATIONS

Life Sciences, vol. 34, pp. 2957 to 2603 (1984).

Primary Examiner—Jeffrey E. Russel
Attorney, Agent, or Firm—Herbert Dubno; Jonathan Myers

[57] ABSTRACT

The present invention relates to novel pentapeptide of formula

Xaa Glu Asp Ser Gly   (SEQ ID NO: 1)

wherein Xaa is pyro-alpha-aminoadipic acid, having specific inhibiting effect on epidermal cell proliferation, salts thereof, pharmaceutical compositions comprising the same and a method for the treatment of mammals for inhibiting the epidermal cell proliferation by administering the novel pentapeptide. The invention also covers a process for the preparation of both the pentapeptide and the pharmaceutical composition.

3 Claims, No Drawings

PENTAPEPTIDE HAVING SPECIFIC INHIBITING EFFECT ON EPIDERMAL CELL PROLIFERATION, THE SALTS THEREOF, PHARMACEUTICAL COMPOSITIONS COMPRISING THE SAME AND A PROCESS FOR THE PREPARATION OF THE PENTAPEPTIDE AND THE PHARMACEUTICAL COMPOSITIONS

TECHNICAL FIELD

The present invention relates to a novel pentapeptide of formula

Xaa Glu Asp Ser Gly                 Sequence No. 1 wherein pAad represents the acyl group of pyro-alpha-amino adipic acid, having specific inhibiting effect on epidermal cell proliferation, salts thereof, pharmaceutical compositions comprising the same and a process for the preparation of the pentapeptide and the pharmaceutical compositions.

BACKGROUND

It is known that the cause of a great part of the dermatological diseases (psoriasis, malignant and benign tumors) is the irregularly enhanced proliferation of epidermal cells. Though several cytostatic drugs are available, their common feature and drawback is that they are toxic and are not specific for the cells of the organ or tissue where the irregular proliferation occurs.

The existence of endogenous substances specifically inhibiting the cell proliferation was supposed at the beginning of the 1960s when tests were carried out in order to determine how the organs of the adult humans and animals can keep their constant size. The compounds ensuring the equilibrium between the inhibition and proliferation of cells were called chalones A-4762-67/539 KY (Biol. Rev., 37, 307 (X1962X).

The chalones are produced in the cells of tissues, thus they paracrinally exhibit their effect by the so-called negative feed-back mechanism. Since then these substances have been isolated from various tissues (mouse skin, rat medulla, human leucocytes, mouse liver, mouse intestine) and the tests carried out on them seem to support the above chalon-hypothesis: the cell proliferation inhibiting effect of these compounds is strictly specific and reversible.

Today the chemical structure of the numerous inhibitors of chalone type is known. All of these substances are peptides.

The structure of the epidermal inhibitor pentapeptide (EI) was discovered in the middle of the 1980's (Cell. Biol. Int. Rep. 8, 379 (1984); Biological Regulation of Cell Proliferation, Eds. R. Baserga et al., Raven Press, N.Y. 1986, Vol. 34, page 259). The amino acid sequence of this peptide is as follows:

Xaa Glu Asp Ser Gly                 Sequence No. 2 wherein Xaa is pyroglutamic acid.

Both the natural and synthetic peptides inhibit the epidermal cell proliferation of mice even in a very small dose ($10^{-14}$ to $10^{-11}$ mol/animal). In vitro it reduces the proliferation rate of mouse epidermal cells by about 40% when administered in a dose of $10^{-12}$ to $10^{-8}$ mol/l.

It is evident that this compound potentially may be a drug for the specific treatment of dermatological diseases caused by epidermal cell proliferation and tumors of other epidermal origin.

The data of structure-activity relationship available up to now show that the activity is highly connected with the structure of EI.

However it was found that the replacement of the N-terminal pyroglutamic acid of the peptide by pyro-alpha-aminoadipic acid had not influenced the cell proliferation inhibiting activity thereof.

The change of pyroglutamic acid to pyro-alpha-amino adipic acid in biologically active peptides is not unprecedented in the prior art. Generally this substitution results in keeping of the biological activity or—in certain cases—some increase of the activity (German published patent application No. 2,514,381, Hungarian patent No. 180,926 and German patent No. 3,226,242; Life Sci., 34, 2597 (1984).

However, an even more significant advantage of the peptide analogues obtained in this manner is that they are less sensitive to peptide degrading enzymes, thus their effect is more durable.

Namely, it is known that the main route of metabolism and inactivation of pyroglutamyl peptides is the splitting off of the pyroglutamyl moiety by the pyroglutamyl-aminopeptidase enzyme. The peptides containing a N-terminal pyro-alpha-aminoadipic acid are resistant to this enzyme.

From these facts, the difference in the strength and duration of the activity, i.e. the inhibition of the proliferation of the epidermal but malignous (so-called HeLa) cells, by the pyro-alpha-aminoadipyl analogoue of the invention, as compared to the known peptide, is surprising and preferable from practical points of view.

The inhibitory effect of the compound of the present invention on the proliferation of tumorous cells is twofold compared to the natural peptide and this effect is maintained even after 13 hours. Considering that the proliferation of healthy epidermal cells is inhibited by both peptides in the same degree, the inhibiting effect of the peptide of the invention is significantly more selective than that of the known one. The increase of selectivity could not have been expected in the knowledge of the prior art.

The novel peptide of sequence No. 1 can be prepared by any method conventionally used in peptide chemistry. For the synthesis of the peptide the stepwise strategy and the benzyl/tert-butyl-type protecting group combination were preferably employed.

This latter means that the alpha-amino groups are temporarily protected by protective groups of benzyl type which can selectively be removed by hydrogenolysis, while the permanent protection of other functional groups is ensured by protective groups of t-butyl type which are split off at the end of the synthesis in one step by acidolysis.

According to a preferred embodiment of the process glycine-t-butyl ester is condensed with N-benzyloxycarbonyl-O-t-butyl-L-serine to form a protected dipeptide of formula Z-Ser('Bu)-Gly-(O'Bu) in the presence of dicyclohexyl carbodiimide, from which the amino protective group is removed by catalytic hydrogenation.

The free dipeptide ester obtained is acylated with N-benzyloxycarbonyl-L-asparaginyl-alpha-(1-hydroxysuccinimidyl)-beta-(t-butyl)-ester to receive the protected tripeptide of formula Z-Asp(O'Bu)-Ser('Bu)-Gly-O'Bu.

The benzyloxycarbonyl protective group is removed by hydrogenolysis again, the amino group liberated is acylated by -benzyloxycarbonyl-L-glutamic acid-alpha-(1-hydroxy-succinimidyl)-gamma-(t-butyl)-ester.

The protected tetrapeptide of Sequence No. 3 which is Glu Asp Ser Gly wherein the gamma glutamyl and beta aspartyl carboxy groups are esterified by t-butyl, the serine hydroxy group is etherified by t-butyl, the glycine carboxy group is esterified by t-butyl, and the glutamic acid amino terminal is blocked by benzyloxy carbonyl is subjected to catalytic hydrogenation and the free tetrapeptide ester thus obtained is acylated with L-pyro-alpha-aminoadipic acid-pentafluorophenyl ester.

From the protected pentapeptide the t-butyl groups are removed in one step by trifluoroacetic acid treatment, thus the novel compound of sequence No. 1 is obtained which is purified by recrystallization from aqueous alcoholic medium. The compound thus obtained is suitable for pharmaceutical use.

In the in vitro test of the cell proliferation inhibiting effect of the new compound of the invention, normal diploid Chang and epidermal HeLa-S3 tumor cell lines were used.

In order to verify the specificity of the effect, the tests were also carried out by using non-target rat medulla and rat thymus cell lines.

The effect on cell proliferation was tested by measuring the incorporation of labelled thymidine.

The in vitro toxicity of the new compound was examined by $^{51}Cr$ emission test.

The cell cultures were developed as follows:

Monolayer cultures of normal diploid epidermal cells

A suspension of epidermal cells containing $2 \times 10^5$ cells/ml was grown in Parker medium supplemented with 10% fetal calf serum. The elements adhered after 24 hour pre-incubation were treated with the active ingredient, then cultured for further 4 hours, treated with 0.12% trypsin, then worked up.

He-La-S3 cell cultures

An aneuploid tumorous cell suspension containing $5 \times 10^4$ to $2.5 \times 10^5$ cells/ml, derived from endometry, was grown in TC-199 Parker medium (product of OKI) supplemented with 10% fetal calf serum in Bellacotubes. The treatment was carried out after 24 hour pre-incubation, 4 hours later the cells were subjected to trypsin treatment and worked up.

Short-term culture of rat medulla cells

After decapitation the femoral medulla was removed from two-week old rats weighing 40 g, then it was suspended in TC-199 Parker medium (product of OKI) supplemented with 10% fetal calf serum. The samples taken from the suspension containing $3 \times 10^6$ cytoblastic cells/ml were incubated with and without the test substances in blood tubes at a temperature of 37° C. under an atmosphere saturated with vapour, comprising 5% by volume carbon dioxide for 4 hours in a Heraaeus B 5060 EK incubator.

Rat thymus cell culture

The rat thymus cells were removed from male rats weighing 40 g after decapitation. The $5 \times 10^6$ cells/ml suspension was cultured for 4 hours in blood tubes, then worked up.

$^{51}Cr$-emission test $6 \times 10^7$ cytoblastic medulla cells to be labelled were centrifuged (1000 rotations/minute for 7 minutes), then the cells were suspended in 1 ml of TC-199 Parker medium (product of OKI) and incubated with $^{51}Cr$ ray source of an activity of $3.7 \times 10^7$ Bq (1 mCi) at a temperature of 37° C. for 1 hour, then the labelled cells were washed with 60 ml of medium. When the evaluation was carried out, the cell suspension was centrifuged after the treatment with the oligopeptide and the radioactivity of the supernatant was measured.

Working up of the cultures

In the 3rd and 12th hour of incubation 36 kBq/ml of $^3H$-Tdr tritiated thymidine (product of UWVR), of a specific activity of 721 MBq/ml were added. 60 minutes later $2 \times 100/ \mu l$ aliquote samples were pipetted to 3 MM filter paper discs (Whatman) and the paper discs were successively washed with ice-cold 5% perchloric acid solution, ethanol and diethyl ether for 5-5 minutes, respectively, then dried.

The radioactivity of the paper discs was measured in a mixture comprising 5 g/ml of 2,5-diphenyl oxazole and 0.3 g/l of 1,4-bis(2-(5-phenyl)-oxazolyl)-benzene in a liquid scintillation spectrometer of Packard-TriCarb type. The number of entries per minute was counted (cpm).

The table shows the latter number, the standard error ($\pm SE$) and the percentage change of the number of entries compared to the control.

When the $^{51}Cr$ emission test was evaluated, the cell suspension was treated with the oligopeptide and centrifuged, then the activity of the supernatant was determined by a Packard apparatus.

The results relating to the effect on cell proliferation of the compound of the invention are summarized in the following tables. The compound of the invention is designated pAad-EI, while the epidermal inhibitor isolated from mouse, used for comparison is designated EI.

TABLE 1

Effect of EI and pAad-EI on the proliferation of Chang-cells Incorporation of $^3H$-thymidine

| concentration /mol/l/ | EI cpm ± SE | | % | pAad-EI cpm ± SE | | % |
|---|---|---|---|---|---|---|
| control | 2567 | 486 | 0 | 1572 | 51 | — |
| $10^{-14}$ | | | | 1099 | 99 | −30.1 |
| $10^{-12}$ | | | | 1176 | 101 | −25.2 |
| $10^{-10}$ | | | | 1346 | 149 | −14.4 |
| $10^{-9}$ | | | | 1310 | 147 | −16.8 |
| $10^{-8}$ | 1552 | 264 | −40 | 1377 | 51 | −12.4 |
| $10^{-6}$ | 1425 | 200 | −44 | 1472 | 56 | −6.3 |
| $10^{-4}$ | 1746 | 210 | −31.3 | 1450 | 51 | −7.8 |

TABLE 2

Effect of EI and pAad-EI on the proliferation of tumorous HeLaS3 cells Incorporation of $^3H$-thymidine

| concentration /mol/l/ | EI 4 hours | | pAad-EI 4 hours | | 13 hours | |
|---|---|---|---|---|---|---|
| | cpm | % | cpm | % | cpm | % |
| control | 413 | — | 15740 | — | 5180 | — |
| $10^{-12}$ | 330 | −20 | 680 | −95.7 | 2420 | −53.3 |
| $10^{-9}$ | 210 | −49 | 2240 | −85.8 | 710 | −86.3 |
| $10^{-6}$ | 253 | −39 | 2930 | −81.2 | 920 | −82.2 |
| $10^{-4}$ | 243 | −41 | 3590 | −77.2 | 6230 | +20.3 |

TABLE 3

Effect of pAad-EI on the proliferation of rat medulla and thymus cells
Incorporation of $^3$H-thymidine

| concentration /mol/l/ | medulla cpm ± SE | | % | thymus cpm ± SE | | % |
|---|---|---|---|---|---|---|
| control | 1165 | 74 | — | 2074 | 236 | — |
| $10^{-14}$ | 1264 | 39 | +13.6 | 2031 | 128 | −2.1 |
| $10^{-12}$ | 1351 | 53 | +16 | 2030 | 76 | −2.2 |
| $10^{-10}$ | 1282 | 85 | +10.1 | 2339 | 129 | +8 |
| $10^{-8}$ | 1267 | 74 | +8.8 | 2039 | 108 | −1.7 |
| $10^{-6}$ | 1160 | 198 | −0.5 | 2196 | 163 | +5.9 |
| $10^{-4}$ | 1190 | 166 | +2.2 | 2311 | 188 | +11.4 |
| $10^{-3}$ | 1130 | 85 | −3 | 2164 | 84 | +4.3 |

TABLE 4

Effect of pAad-EI on the $^{51}$Cr-emission of cytoblastic medulla cells

| | cpm ± SE | |
|---|---|---|
| control | 155,849 | 27,738 |
| concentration = $10^{-8}$ mole/l | 148,303 | 7,976 |

The results summarized in the above Tables clearly support that pAad-EI effectively inhibits the proliferation of epidermal target cells (Table 1 and 2). The extent of the inhibition of the tumorous HeLa cells and the long duration of the effect are remarkable.

The specificity of the effect is verified by the fact that the inhibiting activity is not exerted on non-target (medulla, thymus) cells (Table 3).

The $^{51}$Cr emission tests support that pAad-EI is not toxic as it did not cause higher isotope emission than the control (Table 4).

The further details of the process of the invention are illustrated by the following, non-limiting example.

The abbreviations used in the example correspond to those recommended by the IUPAC-IUB Comission on Chemical Nomenclature (J. Biol. Chem., 247, 977/1972/).

The further abbreviations are as follows:
Z = benzyloxycarbonyl group
Boc = t-butoxycarbonyl group
pAad = pyro-alpha-aminoadipic acid All of the amino acids are of L configuration, if it is not otherwise mentioned.

The melting points were measured with a dr. Tottoli apparatus (product of Büchi).

The optical rotation was determined by a polarimeter of Perkin-Elmer type.

The thin-layer chromatograms were prepared on precoated silica gel plates (Merck; layer thickness: 0.25 mm).

The following solvent mixtures were used for elution (the ratios are expressed in volume):
1) ethyl acetate-pyridine:acetic acid:water (20:6:11) = 99:1
2) ethyl acetate-pyridine:acetic acid:water (20:6:11) = 9:1
3) ethyl acetate-pyridine:acetic acid:water (20:6:11) = 4:1
4) ethyl acetate:n-butanol:acetic acid:water = 1:1:1:1

For the visualization of the thin-layer chromatograms ninhydrine or chlorotolidine/potassium iodide was used.

The solutions were evaporated in vacuo in a Rotavapor "R" (Büchi) vacuum evaporator at a temperature lower than 50° C.

EXAMPLE 1

Xaa Glu Asp Ser Gly        Sequence No. 1 where Xaa is pyroalpha amino adipic acid

Ser($^t$Bu)-Gly-O$^t$Bu-oxalate 2.52 g (15 mmoles) of H-Gly-O$^t$Bu.HCl and 4.43 g (15 mmoles) of Z-Ser($^t$Bu)-OH are dissolved in 30 ml of dichloro methane, then 2.1 ml (15 mmoles) of triethyl amine are added to the solution.

The solution is cooled to a temperature of 0° C. and 3.1 g (15 mmoles) of dicyclohexyl carbodiimide are added under stirring. The reaction mixture is left to stand overnight in a refrigerator, then the precipitate is filtered off and the filtrate is evaporated.

The evaporation residue is dissolved in 100 ml of ethyl acetate and the solution is successively extracted with 2×30 ml of 1N sodium hydrocarbonate solution and with 30 ml of water, dried over anhydrous sodium sulfate and evaporated.

The oily Z-Ser($^t$Bu)-Gly-O$^t$Bu obtained as evaporation residue and 1.9 g (15 mmoles) of oxalic acid dihydrate are dissolved in 200 ml of ethanol and hydrogen gas is bubbled through the solution in the presence of 1 g 10% palladium-on-charcoal catalyst. 1 hour later the catalyst is filtered off, the filtrate is evaporated, the crystalline residue is mixed with ether and filtered off.

Thus 4.52 g (83%) of chromatographically pure Ser($^t$Bu)-Gly-O$^t$Bu-oxalate are obtained.

Melting point: 152°–154° C.

$R_f^3$: 0.21.

Z-Asp(O$^t$Bu)-Ser($^t$Bu)-Gly-O$^t$Bu 4.37 g (12 mmoles) of H-Ser($^t$Bu)-Gly-O$^t$Bu oxalate are dissolved in 30 ml of dichloromethane, then 3.36 ml (24 mmoles) of triethyl amine and 5.46 g (13 mmoles) of Z-Asp(O$^t$Bu)-Osu are added. The reaction mixture is stirred at room temperature overnight, then evaporated.

The evaporation residue is taken up with 100 ml of ethyl acetate, the successively shaken with 30 ml of 1N hydrochloric acid solution, 3×30 ml of 1N sodium hydrocarbonate solution and 30 ml of water. The ethyl acetate solution is dried over anhydrous sodium sulfate, evaporated and the evaporation residue is crystallized by the addition of n-hexane.

Thus 6.1 g (88%) of Z-Asp(O$^t$Bu)-Ser($^t$Bu)-Gly-O$^t$Bu are obtained.

Melting point: (86) . . . 92° C.

$R_f^1$: 0.68.

$(\alpha)^{25}$D: −8.9° (c=1, methanol).

H-Asp(O$^t$Bu)-Ser($^t$Bu)-Gly-O$^t$Bu oxalate 2.81 g (4.85 mmoles) of Z-Asp(O$^t$Bu)-Ser($^t$Bu)-Gly-O$^t$Bu and 0.63 g (5 mmoles) of oxalic acid dihydrate are dissolved in 50 ml of methanol. 0.4 g of 10% palladium-on-charcoal catalyst is suspended in the solution, and hydrogen gas is bubbled through the suspension with stirring for 1 hour.

Then the catalyst is filtered off, the filtrate is evaporated and the evaporation residue is crystallized by the addition of 20 ml of diisopropyl ether. After filtering 2.46 g of crude title product are obtained which is filtered off after mixing with 20 ml of ethyl acetate.

Thus 2.2 g (85%) of H-Asp(O$^t$Bu)-Ser($^t$Bu)-Gly-O$^t$Bu are obtained.

Melting point: 140°–142° C.

$R_f^2$: 0.30.

$(\alpha)^{25}D$: +7.35° (c=1, methanol).

Glu Asp Ser Gly    Sequence No. 3 wherein the gamma glutamyl and beta aspartyl carboxy groups are esterified by t-butyl, the serine hydroxy group is etherified by t-butyl, the glycine carboxy group is esterified by t-butyl, and the glutamic acid amino terminal is blocked by benzyloxy carbonyl.

1.95 g (3.65 mmoles) of H-Asp(O$^t$Bu)-Ser($^t$Bu)-Gly-O$^t$Bu oxalate are shaken between 30 ml of ether and 10 ml of 20% potassium hydrocarbonate solution. The etheral solution is washed with 10 ml of water, dried over anhydrous sodium sulfate and evaporated.

The 1.65 g of oil obtained as evaporation residue and 1.65 g (3.8 mmoles) of Z-Glu(O$^t$Bu)-OSu are dissolved in 20 ml of dichloromethane and the solution is left to stand overnight. Thereafter the solution is evaporated, the evaporation residue is dissolved in 50 ml of ether and the etheral solution is successively shaken with 20 ml of 1N hydrochloric acid solution, 2×20 ml of 1N sodium hydrocarbonate solution and 20 ml of water, dried over anhydrous sodium sulfate and evaporated. The crystalline residue is mixed with ether and left to stand overnight in a refrigerator.

Next day the crystals are filtered off, thus 2.06 g (74%) of Sequence 3 are obtained which is a chromatographically pure, white substance.

Melting point: 124°-126° C.
R$_f^1$: 0.68.
$(\alpha)^{25}D$: -21.0° (c=1, methanol).

Glu Asp Ser Gly as the oxalate Sequence 4 where the gamma-Glu and beta-Asp COOH groups are esterified by t-butyl, the Ser OH group is etherified by t-butyl, and the Gly COOH group is esterified by t-butyl.

1.53 g (2 mmoles) of Sequence 3 and 0.26 g (2 mmoles) of oxalic acid dihydrate are dissolved in 40 ml of methanol, then 0.3 g of palladium-on-charcoal catalyst is suspended in the solution. Thereafter hydrogen gas is led into the solution with stirring for 1 hour.

Then the catalyst is filtered off, the filtrate is evaporated, the evaporation residue is crystallized by the addition of n-hexane, then filtered off.

Thus 1.30 g (90%) of the oxalate of the tetrapeptide of Sequence 4 are obtained.

Melting point: 146°-148° C.
R$_f^2$: 0.24.
R$_f^3$: 0.40.
$(\alpha)^{25}D$: -2.8° (c=1, methanol).

Xaa Glu Asp Ser Gly    Sequence 5 where Xaa is pyro-alpha-amino adipic acid, the gamma-Glu and beta-Asp COOH groups are esterified by t-butyl, the Ser OH is etherified by t-butyl and the Gly COOH group is esterified by t-butyl.

1.08 g (1.5 mmoles) of Sequence 4 are suspended is 15 ml of ether and the suspension is shaken with 10 ml of 20% potassium hydrocarbonate solution until a homogeneous solution is obtained.

The etheral solution is washed with 10 ml of water, dried over anhydrous sodium sulfate and evaporated.

The 0.97 g of oily evaporation residue and 0.5 g (1.62 mmoles) of pAad-Opfp are dissolved in 10 ml of dichloromethane, the solution is diluted with 10 ml of dichloromethane after 1 hour standing, then successively shaken with 3×10 ml of 1N sodium hydrocarbonate solution and 2×10 ml of water. The dichloromethane solution is dried over anhydrous sodium sulfate and evaporated, the evaporation residue is crystallized by the addition of 10 ml of ether and left to stand overnight in a refrigerator.

Next day the precipitate is filtered off, thus 0.88 g (78%) of a chromatographically pure sequence 5 are obtained.

Melting point: 184°-185° C.
R$_f^2$: 0.45.
$(\alpha)^{25}D$: -21.0° (c=1, methanol).

Xaa Glu Asp Ser Gly    Sequence 1;

0.80 g (1.06 mmoles) of Sequence 5 are dissolved in 10 ml of trifluoroacetic acid. After standing for 3 hours the solution is diluted with 50 ml of ether, the precipitate is filtered off and thoroughly washed with ether.

The 0.6 g of crude product obtained is dissolved in 20 ml of water, clarified by the addition of charcoal and the water-clear solution is evaporated. The thick aqueous solution thus obtained is diluted by the addition of 10 ml of ethanol, the precipitate is filtered off and washed with ethanol.

Thus 0.27 g (48%) of the named product are obtained which is a chromatographically pure, white, amorphous substance.

R$_f^4$: 0.31.
$(\alpha)^{25}D$: -47.2° (c=1, methanol).
Amino acid analysis: Aad=0.97 (1); Glu=1.00 (1); Asp=1.00 (1) Ser=0.81 (1); Gly=1.17 (1).

EXAMPLE 2

Injectable powder ampoule 500 mg pentapeptide of Sequence 1 and 9.5 g of lactose are dissolved in 80 ml of distilled water suitable for preparing injections, 0.1 g of methyl-p-hydroxy benzoate are added to the solution, then the volume of the solution is supplemented with distilled water of a quality of suitable for making up injections to 100 ml.

The homogeneous solution is filtered to sterile, each 1 ml is filled into closable vials and the vials are covered with a polymer plug.

Thus powder ampoules containing 5 mg of active ingredient are obtained.

If powder ampoules containing different amount of active ingredient are aimed to be prepared, the amount of lactose is preferably choosen to supplement the weight of the active ingredient to about 10 g calculated for 100 ml of solution. Instead of lactose the same amount of mannitol may also be used.

When the drug is administered, the powder is dissolved in aqueous sodium chloride solution to prepare an isotonic solution.

---

I claim:

1. Xaa Glu Asp Ser Gly Seq. No. 1, wherein Xaa is pyro-alpha-aminoadipic acid, and the salts thereof.

2. Epidermal cell proliferation inhibiting composition for inhibiting tumorous HelaS3 epidermal cells which comprises the novel pentapeptide of formula Xaa Glu Asp Ser Gly          Seq. No. 1 wherein Xaa is pyro-alpha-aminoadipic acid, or the pharmaceutically acceptable salt thereof together with one or more pharmaceutically acceptable inert carriers and/or diluents.

3. Process for the treatment of inhibiting tumorous HeLaS3 the epidermal cell proliferation of mammals which comprises administering to mammals, including humans an effective dose of Xaa Glu Asp Ser Gly          seq. No.1 wherein Xaa is pyro-alpha-aminoadipic acid, or the pharmaceutically acceptable salt thereof per se or in the form of a pharmaceutical composition.

* * * * *

SEQUENCE LISTING ( 1 ) GENERAL INFORMATION:

(  i i i ) NUMBER OF SEQUENCES: 5

( 2 ) INFORMATION FOR SEQ ID NO:1:

( i ) SEQUENCE CHARACTERISTICS:
     ( A ) LENGTH: 5 amino acids
     ( B ) TYPE: amino acid
     ( D ) TOPOLOGY: linear ( i i ) MOLECULE TYPE: peptide ( i x ) FEATURE:
     ( A ) NAME/KEY: Peptide
     ( B ) LOCATION: 1
     ( D ) OTHER INFORMATION: /label=SEQ 1
      / note="Xaa is pyro-alpha-amino adipic acid"

( x i ) SEQUENCE DESCRIPTION: SEQ ID NO:1:

Xaa Glu Asp Ser Gly
1         5

( 2 ) INFORMATION FOR SEQ ID NO:2:

( i ) SEQUENCE CHARACTERISTICS:
     ( A ) LENGTH: 5 amino acids
     ( B ) TYPE: amino acid
     ( D ) TOPOLOGY: linear ( i i ) MOLECULE TYPE: peptide ( i x ) FEATURE:
     ( A ) NAME/KEY: Peptide
     ( B ) LOCATION: 1
     ( D ) OTHER INFORMATION: /label=Seq 2
      / note="Xaa is pyroglutamic acid"

( x i ) SEQUENCE DESCRIPTION: SEQ ID NO:2:

Xaa Glu Asp Ser Gly
1         5

( 2 ) INFORMATION FOR SEQ ID NO:3:

( i ) SEQUENCE CHARACTERISTICS:
     ( A ) LENGTH: 4 amino acids
     ( B ) TYPE: amino acid
     ( D ) TOPOLOGY: linear ( i i ) MOLECULE TYPE: peptide ( i x ) FEATURE:
     ( A ) NAME/KEY: Peptide
     ( B ) LOCATION: 1..4
     ( D ) OTHER INFORMATION: /label=Seq 3
      / note="the gamma-Glu, beta-Asp & Gly COOHs are
      blocked by t- butyl, the Ser OH is blocked by
      t-butyl, & the Glu amino is blocked by ( x i ) SEQUENCE DESCRIPTION: SEQ ID NO:3:

Glu Asp Ser Gly
1

( 2 ) INFORMATION FOR SEQ ID NO:4:

( i ) SEQUENCE CHARACTERISTICS:
     ( A ) LENGTH: 4 amino acids
     ( B ) TYPE: amino acid
     ( D ) TOPOLOGY: linear ( i i ) MOLECULE TYPE: peptide ( i x ) FEATURE:
     ( A ) NAME/KEY: Peptide
     ( B ) LOCATION: 1..4
     ( D ) OTHER INFORMATION: /label=Seq 4
      / note="The gamma-Glu, beta-Asp, & Gly COOHs are blocked by t- butyl, & the Ser OH is blocked by
t-butyl, in the form of the oxalate salt."

( x i ) SEQUENCE DESCRIPTION: SEQ ID NO:4:

Glu Asp Ser Gly
1

( 2 ) INFORMATION FOR SEQ ID NO:5:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1..5
( D ) OTHER INFORMATION: /label=Seq 5
/ note="the Xaa is pyro-alpha-amino adipic acid,
the gamma- Glu, beta-Asp & Gly COOHs are blocked by
t-butyl, and the Ser OH is blocked by t-butyl."

( x i ) SEQUENCE DESCRIPTION: SEQ ID NO:5:

Xaa Glu Asp Ser Gly
1               5